United States Patent
Yeatman

(10) Patent No.: US 6,451,029 B1
(45) Date of Patent: Sep. 17, 2002

(54) INTESTINAL STAPLING DEVICE AND METHOD

(75) Inventor: Timothy J. Yeatman, Tampa, FL (US)

(73) Assignee: University of South Florida, Tampa, FL (US)

( * ) Notice: Subject to any disclaimer, the term of this patent is extended or adjusted under 35 U.S.C. 154(b) by 72 days.

(21) Appl. No.: 09/643,299

(22) Filed: Aug. 22, 2000

Related U.S. Application Data

(60) Provisional application No. 60/150,222, filed on Aug. 23, 1999.

(51) Int. Cl.$^7$ ............................................. A61B 17/115
(52) U.S. Cl. ....................... 606/139; 606/153; 606/213; 227/175.1
(58) Field of Search ............................ 606/1, 139, 142, 606/153, 219, 213; 227/175.1–175.4, 176.1, 177.1, 178.1, 179.1, 180.1, 181.1, 182.1, 901

(56) References Cited

U.S. PATENT DOCUMENTS

| | | | |
|---|---|---|---|
| 5,309,927 A | * | 5/1994 | Welch .......................... 128/898 |
| 5,350,355 A | * | 9/1994 | Sklar ............................. 604/23 |
| 5,533,661 A | * | 7/1996 | Main et al. ............... 227/176.1 |

* cited by examiner

Primary Examiner—David O. Reip
(74) Attorney, Agent, or Firm—Saliwanchik, Lloyd & Saliwanchik

(57) ABSTRACT

A stapler and associated methods for joining resected passageways together and leak testing the anastomosis is described, the stapler including an elongated member for insertion adjacent two sections of tissue desired to be joined. At the distal end of the elongated member is positioned tissue-joining apparatus, which is activated from adjacent the proximal end. The elongated member has a lumen extending from adjacent the distal end to adjacent the proximal end. A method of the present invention includes leak testing the anastomosis with the same instrument that was used for joining the tissue sections together by introducing air through the lumen from the proximal end to the distal end to perform insufflation. A further aspect of the method comprises the step of facilitating the instrument's insertion into a passageway prior to tissue joining by insufflating the passageway if it is in a collapsed state.

9 Claims, 1 Drawing Sheet

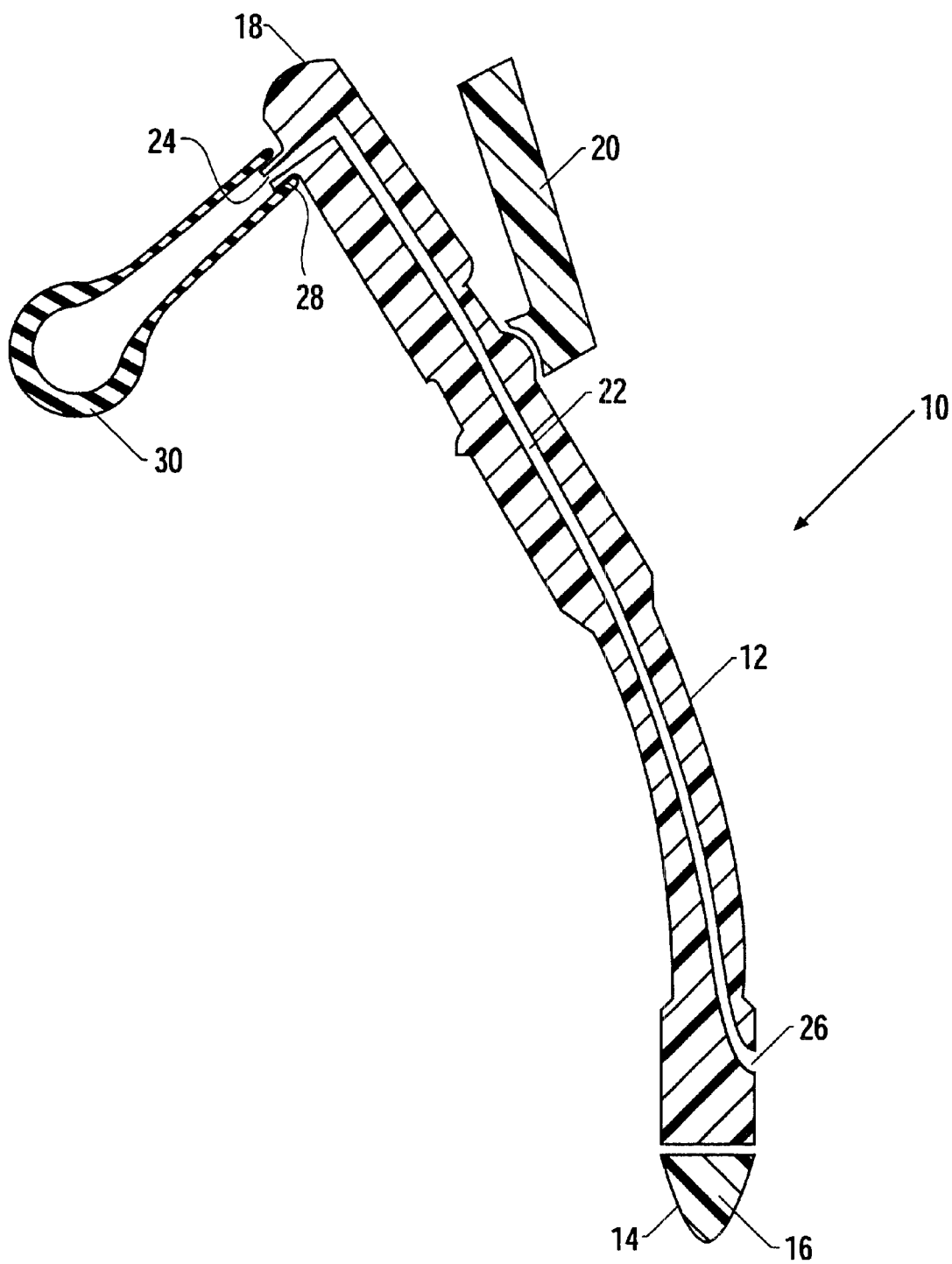

INTESTINAL STAPLING DEVICE AND METHOD

CROSS-REFERENCE TO RELATED APPLICATION

This application claims priority from Provisional Application No. 60/150,222, filed Aug. 23, 1999, entitled "Intestinal Stapling Device and Method," both of which are commonly owned.

BACKGROUND OF THE INVENTION

1. Field of the Invention

The present invention relates to surgical devices and methods, and, more particularly, to such devices and methods for stapling a resected passageway together.

2. Description of Related Art

Low anterior bowel resection is a procedure typically used to treat colon or rectal cancer. One of the most serious complications following this procedure is the development of a leak from the anastomosis, which is the region at which the two cut sections of the passage are joined together end to end. Leaks following the resection of, for example, distal rectal lesions can result in death or at minimum prolonged or permanent colostomy, with great expenditure incurred in additional hospital days and medication.

Despite the known potential complications, little progress has been made in alleviating this problem, as leak rates have remained constant. Leaks may be caused by a number of factors, including poor blood supply, tension, or holes/defects in the staple lines. Currently used stapling devices, such as the Endopath Proximate ILS Curved Intraluminal Stapler, do not permit testing for leaks; rather, the device must be removed and another device such as a rigid proctoscope inserted to permit air insufflation for leak testing.

Another problem associated with such procedures is that the stapling device can be difficult to insert into the anus if the rectal vault has collapsed.

SUMMARY OF THE INVENTION

It is therefore an object of the present invention to provide a device that tests an anastomosis for integrity of the joined region.

It is a further object to provide such a device that both staples and performs the leak testing.

It is another object to provide such a device that is insertable into a collapsed orifice.

It is an additional object to provide a method of leak testing an intestinal anastomosis.

It is yet a further object to provide such a method for stapling and leak testing with a common instrument.

It is yet another object to provide such a method for expanding a collapsed orifice to facilitate instrument insertion.

These and other objects are attained with the present invention, a stapler and associated methods for joining resected passageways together and leak testing the anastomosis. The stapler comprises an elongated member having a length sufficient to extend from an area outside a surgical site to a region at the surgical site having two sections of tissue desired to be joined. At the distal end of the elongated member is positioned means for joining the tissue sections together. Means for activating the joining means is positioned adjacent the proximal end.

The elongated member has a lumen extending from adjacent the distal end to adjacent the proximal end. Affixable to an opening at the proximal end of the lumen is means for insufflation for introducing a fluid into the lumen and out through an opening at the distal end of the lumen.

A method of the present invention includes joining two tissue segments together with an instrument and leak testing the anastomosis with the same instrument. A further aspect of the method comprises the step of facilitating the instrument's insertion into a passageway by insufflating the passageway if it is in a collapsed state.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is an axial cross-sectional view of the stapler of the present invention.

DETAILED DESCRIPTION OF THE PREFERRED EMBODIMENTS

A description of the preferred embodiments of the present invention will now be presented with reference to FIG. 1.

The stapler 10 in a particular embodiment is for use in joining resected ends of a rectum or colon. The stapler 10 comprises an elongated section 12 that has at the distal end 14 a stapling means 16 for joining tissue sections such as is known in the art. Adjacent the proximal end 18 is an actuator such as a handle 20 operable to release and close a staple from the stapling means 16, by such means as are known in the art.

The stapler 10 further has an axial lumen 22 extending from a proximal opening 24 adjacent the proximal end 18 to a distal opening 26 adjacent the distal end 14. Extending from the proximal opening 24 is a protrusion 28, affixable to which is an insufflation means such as an air bulb 30.

In use, following the resection procedure, the insertion of the stapler 10 may be facilitated if needed by insufflating a collapsed orifice, for example, the rectum. The insufflation is accomplished by inserting the distal end 14 of the stapler 10 until the distal opening 26 is within the passageway and a seal is created by the tissue (e.g., the anal sphincter) surrounding the instrument 10. The bulb 30 is affixed to the protrusion 28, and air is introduced into the lumen 22 therewith, expanding the passageway.

The stapling then proceeds by means known in the art, such as by creating a horizontal staple line and an end-to-end anastomosis. The air bulb 30 is again employed to introduce air into the lumen 22 in order to leak test the stapled regions.

It is anticipated that the present device and method would save approximately 5–10 min in each procedure by permitting a rapid performance of a leak test with the same instrument being used for tissue stapling. Not only is time saved, but less stress is placed on the newly joined tissue anastomoses, since there a second instrument is not required to be introduced and withdrawn following resection, and the use of a rigid proctoscope to perform leak testing would be obviated.

It may be appreciated by one skilled in the art that additional embodiments may be contemplated, including similar instruments for use in other tissue-joining applications wherein leak testing is desirable.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A device for joining two sections of tissue together and for testing an integrity of the joined sections comprising:

an elongated member having a length sufficient to extend into a surgical site to reach two sections of tissue desired to be joined and further having a lumen extending from a distal opening adjacent a distal end to a proximal opening adjacent a proximal end;

means positioned at the elongated member distal end for joining the two sections of tissue together; to form a joined region means for actuating the joining means operatively connected thereto and having an actuating portion movably affixed adjacent the elongated member proximal end; and insufflation means affixable to the proximal opening for introducing a fluid through the lumen and out the distal opening, for performing at least one of an insufflation of the surgical site or a testing of the integrity of the joined region of the two tissue sections.

2. The device recited in claim 1, wherein the joining means comprises means for stapling the two tissue sections together.

3. The device recited in claim 2, wherein the actuating means comprises a handle operatively connected to the stapling means movable between a passive position and a stapling position adapted for activating the stapling means.

4. The device recited in claim 1, wherein the elongated member has a protrusion extending from and in surrounding relation to the proximal opening.

5. The device recited in claim 4, wherein the insufflation means comprises an air bulb affixable in surrounding and fluid-tight relation to the protrusion.

6. A method for joining two sections of tissue together and for testing the integrity of the joined sections comprising the steps of:

inserting into a surgical site an elongated member having a lumen extending from a distal opening adjacent a distal end to a proximal opening adjacent a proximal end;

joining two sections of tissue together using joining means positioned at the elongated member distal end by actuating the joining means from adjacent the elongated member proximal end; and performing at least one of the steps of insufflating the surgical site and testing an integrity of the joined two sections using insufflation means affixable adjacent the elongated member proximal opening.

7. The method recited in claim 6, wherein the joining means comprises a stapler.

8. the method recited in claim 6, wherein the insufflating and testing steps each comprise the steps of:

affixing an air bulb in fluid-tight relation to the elongated member proximal opening;

depressing the air bulb to force air into the elongated member lumen, out the distal opening, and into the surgical site, thereby effecting at least one of insufflation or integrity testing.

9. The method recited in claim 6, wherein the surgical site comprises a lower bowel and the two sections of tissue comprise resected ends of a rectum or a colon.

* * * * *